United States Patent
Hansen

(10) Patent No.: US 11,865,151 B2
(45) Date of Patent: Jan. 9, 2024

(54) LIVE BIOTHERAPEUTICS FOR THE TREATMENT OF CARBOHYDRATE DISORDERS

(71) Applicant: GUTSYBIO INC., San Diego, CA (US)

(72) Inventor: Genevieve Hansen, Rancho Santa Fe, CA (US)

( * ) Notice: Subject to any disclaimer, the term of this patent is extended or adjusted under 35 U.S.C. 154(b) by 576 days.

(21) Appl. No.: 16/792,178

(22) Filed: Feb. 14, 2020

(65) Prior Publication Data

US 2020/0261521 A1    Aug. 20, 2020

Related U.S. Application Data

(60) Provisional application No. 62/972,451, filed on Feb. 10, 2020, provisional application No. 62/805,922, filed on Feb. 14, 2019.

(51) Int. Cl.
| | |
|---|---|
| *A61K 36/06* | (2006.01) |
| *C12N 1/16* | (2006.01) |
| *A23L 33/14* | (2016.01) |
| *A23L 33/00* | (2016.01) |
| *A23L 33/21* | (2016.01) |

(52) U.S. Cl.
CPC .............. *A61K 36/06* (2013.01); *A23L 33/14* (2016.08); *A23L 33/21* (2016.08); *A23L 33/30* (2016.08); *C12N 1/16* (2013.01); *A23V 2002/00* (2013.01)

(58) Field of Classification Search
None
See application file for complete search history.

(56) References Cited

PUBLICATIONS

Liccioli, Tommaso; "Improving fructose utilization in wine yeast using adaptive evolution" Doctoral Thesis, The University of Adelaide, Aug. 2010 (Year: 2010).*
Hong, Kuk-Ki; "Advancing Metabolic Engineering through Combination of Systems Biology and Adaptive Evolution" Doctoral Thesis, Chalmers University of Technology, Aug. 2012 (Year: 2012).*
Brown, CM; Johnson, B; "Influence of the Concentration of Glucose and Galactose on the Physiology of *Saccharomyces cerevisiae* in Continuous Culture" Journal of General Microbiology, 64, 279-287, 1970 (Year: 1970).*
Hong, Kuk-Ki; Nielsen, Jens; "Adaptively evolved yeast mutants on galactose show trade-offs in carbon utilization on glucose" Metabolic Engineering, 16, 78-86, 2013 (Year: 2013).*

* cited by examiner

*Primary Examiner* — David W Berke-Schlessel
(74) *Attorney, Agent, or Firm* — The Law Office of Jane K Babin, PC; Jane K Babin

(57) ABSTRACT

The present invention provides method for treating a metabolic disorder, dietary intolerance, or malabsorption in a subject that causes an excess of a metabolite or a dietary substance, particularly a carbohydrate such as galactose or fructose, that the subject does not tolerate by administering an effective amount of an adaptively evolved yeast strain to the subject or to food that reduces the excess of the metabolite or dietary substance. Specifically, the invention is directed to methods for treating the metabolic disorder, such as galactosemia or fructosemia, in which an excess of the carbohydrate is present. The invention also provides isolated, adaptively evolved yeast strains that degrades a metabolite or dietary ingredient, such as galactose or fructose, and methods for preparing such isolated, adaptively evolved yeast strains.

7 Claims, 1 Drawing Sheet

LIVE BIOTHERAPEUTICS FOR THE TREATMENT OF CARBOHYDRATE DISORDERS

This application claims the benefit of priority under 35 USC § 119 of U.S. Provisional Application Ser. No. 62/805,922, filed Feb. 14, 2019, U.S. Provisional Application Ser. No. 62/972,451, filed Feb. 10, 2020, the entire disclosures of which is incorporated herein by reference.

FIELD OF THE INVENTION

The present invention relates to products and methods for the treatment, or the reduction of the severity of symptoms, associated with rare metabolic disorders, dietary intolerance and malabsorption. Specifically, the invention relates to live biotherapeutics, such as non-engineered microorganisms, including yeast or bacterial strains, selected for their enhanced ability to reduce specific metabolites and/or dietary ingredients in the human gastrointestinal tract and in food that otherwise would cause a disease or disorder in the subject.

BACKGROUND

Dietary Intolerance

Dietary intolerance is a broad clinical condition that affects 15-20% of the population. There are multiple dietary intolerance-related disorders with symptoms and prognosis that vary widely but their chronic nature can have a significant impact on quality of life at best, and can be a life-threatening condition at worst (Lomer M C E. Review article: the aetiology, diagnosis, mechanisms and clinical evidence for food intolerance. *Aliment Pharmacol Ther.* 2015; 41(3): 262-275).

Among subjects suffering from dietary intolerance, carbohydrates are frequently identified as elicitors of gastrointestinal (GI) symptoms with various manifestations such as abdominal bloating, flatulence, pain, distension, diarrhea and nausea. Symptomatic subjects will often undergo a long process of investigations such as endoscopy, imaging studies and blood tests before linking their conditions to dietary carbohydrates and in particular to fructose. The current diagnosis algorithm for dietary fructose-related conditions involves a complete food history review, breath testing for hydrogen production, and eventually removal of the offending carbohydrate from the diet (Rao et al., Ability of the normal human small intestine to absorb fructose: evaluation by breath testing. *Clin Gastroenterol Hepatol.* 2007; 5(8): 959-963).

Fructose is a free monosaccharide naturally present in a variety of foods such as honey, fruits and vegetables, and as a processed product such as high fructose corn syrup. Fructose can bind to other carbohydrates, for instance with glucose to form sucrose in cane sugar and beet sugar. Fructose can also polymerize to form oligo- or polysaccharides such as fructans and as FODMAP (Fermentable Oligo-Di-Monosaccharide and Polyols). Fructose is increasingly used as a sweetening agent in numerous foods and beverages.

Amongst the different forms of fructose, it is the free fructose which most strongly influences fructose intolerance. Free fructose is absorbed directly across the intestinal epithelium by carrier-mediated facilitative diffusion via glucose transport proteins like GLUT-5 and metabolized by fructokinase, aldolaseB, and triokinase enzymes. The majority of fructose is converted into glucose and part of it is converted into lactate and fatty acids. Fructose intolerance or fructose malabsorption occurs when the gut absorptive capacity for fructose is altered and consequently, fructose remains trapped in the lumen of the digestive tract (Ebert K, Witt H. Fructose malabsorption. *Mol Cell Pediatr.* 2016; 3(1):10). The pathophysiology of fructose malabsorption is multifactorial as fructose in the gut acts as an osmotic force causing a rapid influx of fluid into the lumen and a rapid transport of highly osmotic and unabsorbed fructose across the colon. Fructose may then quickly be converted into short-chain fatty acids by the host microbiome in the colon ultimately resulting in fermentation with methane and hydrogen production. The short-chain fatty acids can also contribute to the overall manifestations of gastrointestinal distress by triggering higher motility. In the case of fructans, the mechanism for intolerance can largely be explained by the lack of enzymes to fully hydrolyze fructan glycosidic linkages, leaving significant residual level of fructans with a propensity for water retention and fermentation (Gibson et al., Fructose malabsorption and the bigger picture. *Aliment Pharmacol Ther.* 2007; 25(4):349-363).

It is clear that there are fructose intolerance disorders of different severity and the shift from normal to symptomatic is subject to individual variations. It is also clear that incomplete absorption of free fructose induces dose-dependent gastrointestinal symptoms in a high proportion of patients with functional gut disorders such as IBS and in healthy subjects where the symptoms are generally less severe and less frequent in their occurrence (Shepherd et al., Short-Chain Carbohydrates and Functional Gastrointestinal Disorders. *Am J Gastroenterol.* 2013; 108(5):707-717). Furthermore, it has become clear that high consumption of fructose can lead to a broad spectrum of metabolic disorders including insulin resistance, hyperinsulinemia, hypertension, and dyslipidemia. Recent epidemiological studies have also revealed a correlation between excessive fructose consumption and tumor genesis and progression.

Metabolic Disorders

In addition to malabsorption/intolerance related disorders, dietary carbohydrate (e.g. fructose, galactose) can trigger a broad range of toxic effects on subjects with inborn errors of metabolism (IEM) whose capacity to metabolize a specific carbohydrate is limited.

Metabolic disorders are in many cases triggered by mutated genes that result in enzyme deficiencies. Such enzymes are either not produced at the effective amount or are produced in an altered form. In either case, the alteration of enzyme activity triggers the build-up of certain metabolites that otherwise would not be toxic or necessary by-products are not produced resulting in the onset of the metabolic disorder. There are multiple metabolic disorders and their symptoms, prognosis and treatments vary widely, but their genetic nature, makes them chronic in nature with a significant impact on quality of life at best, and a life-threatening condition at worst in many of the patient subjects.

Galactosemia

Galactosemia or "galactose in the blood" is a rare metabolic disease in which the body cannot break down galactose properly. In patients with galactosemia, galactose builds up to toxic levels in the body causing a range of life-threatening health damage: lack of energy, growth failure, liver and brain damage, bleeding, cataract, possibly serious infections, speech difficulties, and intellectual impairment. Galactosemia Foundation, "What Is Galactosemia?" (n.d.) viewed at www-dot-galactosemia-dot-org/understanding-galactosemia; Lai et al., "Galactose toxicity in animals." IUBMB Life 61:1063-74 (2009).

Galactosemia is an inherited condition occurring in 1 in 30,000 to 60,000 individuals that is caused by a deficiency of any one of three enzymes (galactokinase, galactose-1-phosphase uridyl transferase and UDP-glucose epimerase, illustrated below) involved in the metabolism of galactose. Lai et al., supra; Demirbas et al., "Hereditary galactosemia." Metabolism 83:188-96 (2018); McCorvie et al, "Molecular basis of classic galactosemia from the structure of human galactose 1-phosphate uridylyltransferase." Hum Mol Genet 25:2234-44 (2016).

Galactose is a sugar commonly found in food, which is absorbed across the intestine (Wright et al., "Intestinal absorption in health and disease—sugars." Best Pract Res Clin Gastroenterol 17:943-56 (2003); Gross & Acosta, "Fruits and vegetables are a source of galactose: implications in planning the diets of patients with galactosaemia." J Inherit Metab Dis. 14:253-8 (1991); Gleason et al., "Understanding galactosemia: a diet guide." In: Abbot Nutrition and Abbot Laboratories, Columbus, OH (2010)). Most of the absorbed galactose enters the liver, where it is mainly converted to glucose, which is then either incorporated into glycogen for energy storage or used for energy (Demirbas et al., supra). If infants are found to be galactosemia positive through the newborn screening program, a diet-based treatment is started right away to minimize serious brain damage during the newborn period. Thereafter, as infants grow into children, the diet continues in an attempt to lower blood and organ galactose accumulation (Demirbas et al., supra; Thompson & Netting "Dietary Management of Galactosaemia." ASIEM (2010); Tang et al., "Innovative therapy for Classic Galactosemia—Tale of two HTS." Mol Genetics and Metab 105:44-55 (2012).

Fructosemia

Three IEM are known in the pathway of fructose metabolism: hereditary fructose intolerance (HFI), fructose-1,6-bisphosphatase (FBPase) deficiency, and essential or benign fructosuria due to fructokinase deficiency. In the case of HFI, it is caused by a rare autosomal-recessive inherited disorder with mutations in the aldolase B gene where fructose is either not degraded at all or not in sufficient amounts. Fructose can reach toxic levels leading to severe abdominal symptoms and renal or nervous system toxicity with continued exposure. The incomplete breakdown of fructose in HFI patients leads to an accumulation of biochemically active compounds which deplete cellular ATP. It results in increased uric acid production and decreased protein synthesis which leads to hepatic and renal dysfunction. Prevalence of HFI is estimated to be 1 in 26,100 with a calculated asymptomatic carrier frequency between 1:55 and 1:120. Even minute amount of dietary fructose may be lethal in extreme cases of HFI. Of note, even symptomatic carriers are predisposed to hyperuricemia with high levels of dietary fructose exposure (Tran C. Inborn Errors of Fructose Metabolism. What Can We Learn from Them? *Nutrients.* 2017; 9(4)).

Living with dietary fructose-related disorders is challenging. At this time, there are very few approaches available to address dietary fructose-induced disorders. The current treatment consists of lifelong adherence to dietary modification aimed at minimizing or avoiding fructose-containing foods. Because the absorption capacity for fructose is highly individual, the tolerated dose has to be individually tailored and then the diet has to be customized to be the least restrictive possible while still keeping the array of symptoms under control. While a large percentage of the population is not able to absorb over 25 g of fructose per day, the daily consumption is typically 10 g to 50 g. Even healthy subjects can experience gastrointestinal symptoms after a daily consumption of 25-50 g. There is agreement that 50 g fructose in adults and 2 g/kg fructose in children exceed the absorption capacity for the majority of subjects. A dose of less than 25 g in adults and less than 1 g/kg in children appears to be adequate. As for individuals suffering from fructose intolerance, guidelines published from the Academy for Nutrition and Dietetics suggest daily serving of 3 g of fructose and less than 0.5 g of fructan. For patients with HFI, the daily serving is even more critical due to systemic inability to process fructose with potentially fatal consequences.

Living with a carbohydrate metabolism disorder is challenging. At this time, there are no medications available that lower galactose or fructose levels. The current treatment consists of lifelong adherence to a diet free of the offending carbohydrate.

Diet restriction is however not a practical long-term solution because of the extensive inclusion of offending carbohydrates in foods and beverages. Galactose is commonly found in a range of common foods like milk, beans, nuts, and fruits making compliance with this diet challenging (Galactosemia Foundation, supra; Lai et al., supra; Demirbas et al. supra). Fructose is prevalent in fruits and vegetables.

A diet completely deprived of fructose-containing foods may be unbalanced and may lead to deficiencies with an adverse impact on the overall health status. Specially-manufactured food formulas (e.g. devoid of galactose) are expensive and sometime unaffordable. Alternative and/or complementary approaches are under consideration such as drugs targeting the defective metabolic pathway, but they are still at the development stage (Demirbas et al. supra; Tang et al., supra). Thus, dietary restriction will likely remain the cornerstone of galactosemia and fructosemia management for the foreseeable future. Therefore, there is a need for a long-term and cost-effective solution offering a simple and palatable approach that would allow infants and children to ingest more normal diets.

Lactobacilli are the most common microorganisms resident in the gastrointestinal (GI) tract in humans. In fact, Lactobacilli have been widely used as delivery systems in human GI tract in the form of live biotherapy either as colonizers and/or delivery expression systems for therapeutic molecules. Yeasts represent another group of organisms that have been exploited for potential as live biotherapeutic products given their generally recognized as safe (GRAS) status as well as their potential to restore gut function after long term antibiotic therapy.

SUMMARY OF THE INVENTION

The present invention provides compositions and method for treating dietary intolerance, malabsorption and/or a metabolic disorders in a subject. In one embodiment, a method of the invention comprises administering an effective amount of an adaptively evolved microorganism to the subject or to food containing a metabolite or dietary substance, such as a carbohydrate (e.g., galactose or fructose) that the subject, does not tolerate, cannot metabolize or cannot absorb, where the effective amount of the adaptively evolved microorganism reduces the amount of the metabolite or dietary substance. The microorganism will typically be non-pathogenic when introduced into the gastrointestinal tract of a human and generally recognized as safe ("GRAS"). Administration can be by any suitable route, such as by oral consumption, via a nasogastric tube, an orogastric tube, an enema or an endoscope. In some aspects, the microorganism is enterically coated.

In certain aspects, the adaptively evolved microorganisms of the invention remain viable (at least 50% viability) under a condition present in the gastrointestinal tract, such as a gastric fluid environment, intestinal fluid environment or a gastric fluid environment followed by an intestinal fluid environment. Certain such adaptively evolved microorganisms of the invention can also withstand gastric fluid environment conditions such as simulated gastric fluid at 37° C.; with pepsin, pancreatin and/or bile salts; pH about 2.

The adaptively evolved microorganisms of the invention preferably demonstrates a property required for colonization of the gastrointestinal tract, such as is adherence to gut intestinal cells (e.g. >10% adherence to gut intestinal cells after 90 minutes contact).

In some aspects, the adaptively evolved microorganism is a yeast. Non-limiting examples of yeast suitable for use in the methods of the invention include *Saccharomyces* sp., a *Saccharomyces* sp., a *Kluyveromyces* sp., a *Pichia* sp., and a *Metschnikowia* sp., such as *Saccharomyces cerevisiae*, *Saccharomyces uvarum*, *Kluyveromyces marxianus*, *Pichia kudriavzevii*, and *Metschnikowia reukaufii*.

In certain aspects, the isolated, adaptively evolved microorganism strain degrades a carbohydrate such as galactose or fructose. Suitable galactose degrading strains of the invention include *Saccharomyces cerevisiae* strain Y_C202_1, *Saccharomyces cerevisiae* strain Y_C201_1, or *Kluyveromyces marxianus* strain K_219. Suitable fructose degrading strains include *Pichia kudriavzevii* strain G1_1A, *Saccharomyces cerevisiae* strain G2_1A, *Saccharomyces uvarum* strain G3_1A, or *Metschnikowia reukaufii* strain G4_1A.

The microorganism can be adaptively evolved by a method that include the steps of: growing a microorganism under an adaptive condition for a plurality of microorganism cell generations, wherein the microorganism heritably adapts to the adaptive condition; and confirming heritable adaptation of the microorganism, thereby adaptively evolving the microorganism strain.

Typically, the adaptive condition is the presence of the metabolite or dietary substance that the subject is intolerant of, and the heritable adaptation is degradation of the metabolite or dietary substance. For example, in galactosemia, the metabolite is galactose the adaptive condition is galactose or galactose plus glucose and the adaptation is degradation of galactose in the presence or absence of glucose. Similarly, in the fructose intolerance or fructosemia, the metabolite or dietary substance that the subject is intolerant of is fructose, and the adaptation is degradation of fructose.

The invention also provides isolated, adaptively evolved microbial strains, including but not limited to yeast strains, that degrades a dietary substance or a metabolite. Adaptively evolved yeast strains can be prepared by growing a yeast under an adaptive condition for a plurality of yeast cell generations, where the yeast heritably adapts to the adaptive condition; isolated adapted yeast clones, and confirming heritable adaptation of the yeast, thereby adaptively evolving the yeast strain. The adaptive condition is the presence of the dietary substance or the metabolite (e.g. a carbohydrate such as galactose, galactose plus glucose, or fructose) and the heritable adaptation is degradation of the dietary substance or the metabolite. Strains of the invention disclosed herein including *Saccharomyces cerevisiae* strain Y_C202_1, *Saccharomyces cerevisiae* strain Y_C201_1, and *Kluyveromyces marxianus* strain K_219 are adapted to degrade galactose, even in the presence of glucose. Additional disclosed strains of the invention which are adapted to degrade fructose, include *Pichia kudriavzevii* strain G1_1A, *Saccharomyces cerevisiae* strain G2_1A, *Saccharomyces uvarum* strain G3_1A, and *Metschnikowia reukaufii* strain G4_1A.

Also provided are compositions comprising an isolated, adaptively evolved microbial strain described herein (e.g. yeast strain) and a pharmaceutically acceptable excipient or carrier. Optionally, these composition can be enterically coated.

Also provided are compositions comprising an isolated, adaptively evolved microbial strain (e.g. yeast strain) described herein, and food, such as milk.

The invention also includes methods for adaptively evolving a microorganism for treatment of a carbohydrate-related metabolic disorder, malabsorption or dietary intolerance, including the steps of providing a microorganism; growing the microorganism under an adaptive condition comprising the presence of a carbohydrate (e.g. galactose or fructose), where the organism adapts to the adaptive condition; and confirming adaptation of the microorganism, thereby adaptively evolving the microorganism. These methods may include inoculating a culture medium comprising the adaptive condition with the microorganism; growing the microorganism in the culture medium (e.g., for 20-75 cell generations) thereby preparing an actively growing adaptive culture; diluting the actively growing adaptive culture with fresh medium comprising the adaptive condition; and repeating steps the dilution growth-dilution or process multiple times, such as 10-100 times, at intervals of, for example, 8, 12, 24, 36, 72, more hours. Detecting and confirming the adaptation can include detecting the change in growth efficiency, as measured by changes in generation time, specific growth rate, or doubling time. Such methods can be used to adaptively evolve yeast for the treatment of the metabolic disorders galactosemia and fructosemia, as well as intolerances or malabsorption of galactose and fructose, respectively.

BRIEF DESCRIPTION OF THE DRAWINGS

Serum samples were collected at 0-hour pre-administration and at 0.5, 1, 1.5, 2, 4, and 8-hour post administration (horizontal axis, in hours). FIG. 2A shows fructose concentrations in serum after oral delivery of the test article alone (◇), after oral delivery of 10% fructose alone (□) and after oral delivery of 10% fructose together with the test article (■). FIG. 2B shows fructose concentrations in serum after oral delivery of the test article alone (◇), after oral delivery of 20% fructose alone (○) and after oral delivery of 20% fructose together with the test article (●). Each data point represents means of duplicate values obtained for serum samples collected from three animals per group.

DETAILED DESCRIPTION

Figure 1:
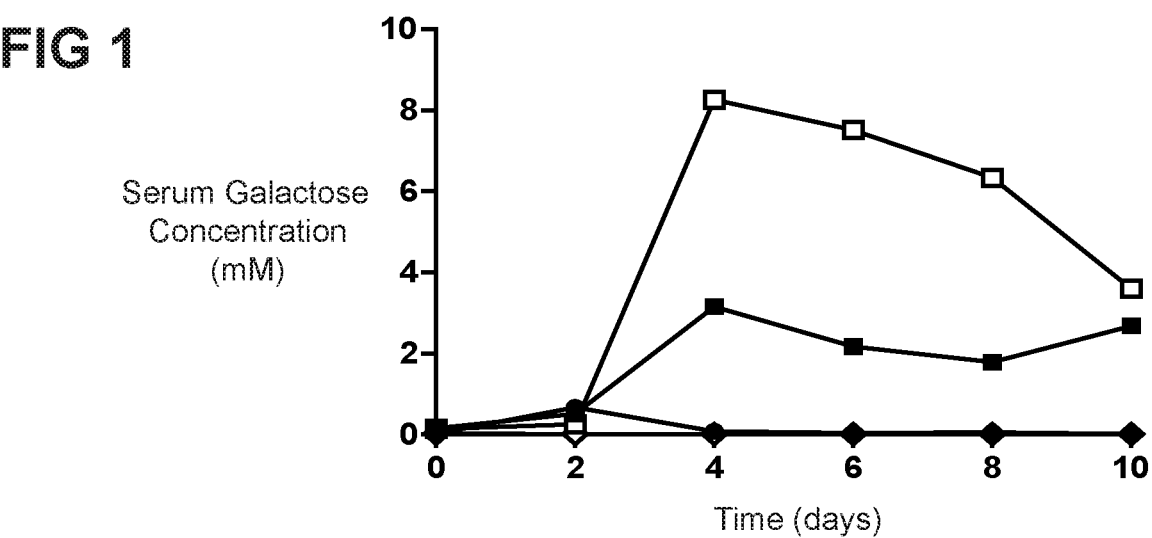
FIG. 1 represents the time course profile of serum galactose concentrations (vertical axis, in mM) after oral administration of galactose with or without the test article collected on Day 0, 2, 4, 6, 8, and 10 of the study (horizontal axis, in day). Four groups of three Sprague-Dawley male rats were dosed via three daily oral gavage administration for 10 Days with (i) PBS while having access ad libitum to 12.5% galactose in drinking water (□), (ii) test article with access to 12.5% galactose in drinking water (■), (iii) test article alone (◇), and (iv) test article delivered concurrently with a solution of 12.5% galactose (●). Each data point represents means of duplicate values obtained for serum samples collected from three animals per group at the indicated time points.

Unless otherwise noted, the terms used herein are to be understood according to conventional usage by those of ordinary skill in the relevant art. In addition to the definitions of terms provided below, definitions of common terms in molecular biology may also be found in Rieger et al. 1991 Glossary of genetics: classical and molecular, 5th Ed., Berlin: Springer-Verlag; and in Current Protocols in Molecular Biology, F. M. Ausubel et al. Eds., Current Protocols, a joint venture between Greene Publishing Associates, Inc. and John Wiley & Sons, Inc., (1998 Supplement).

It is to be understood that as used in the specification and in the claims, "a" or "an" can mean one or more, depending upon the context in which it is used. Thus, for example, reference to "a cell" can mean that at least one cell can be utilized.

Also, for the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Also, for the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Definitions

"About" as used herein means that a number referred to as "about" comprises the recited number plus or minus 1-10% of that recited number. For example, "about" 100 cells can mean 95-105 cells or as few as 99-101 cells depending on the situation. Whenever it appears herein, a numerical range such as "1 to 20" refers to each integer in the given range; e.g., "1 to 20 cells" means 1 cell, 2 cells, 3 cells, etc., up to and including 20 cells. Where about modifies a range expressed in non-integers, it means the recited number plus or minus 1-10% to the same degree of significant figures expressed. For example, about 1.50 to 2.50 mM can mean as little as 1.35 M or as much as 2.75M or any amount in between in increments of 0.01. Where a range described herein includes decimal values, such as "1.2% to 10.5%", the range refers to each decimal value of the smallest increment indicated in the given range; e.g. "1.2% to 10.5%" means that the percentage can be 1.2%, 1.3%, 1.4%, 1.5%, etc. up to and including 10.5%; while "1.20% to 10.50%" means that the percentage can be 1.20%, 1.21%, 1.22%, 1.23%, etc. up to and including 10.50%.

As used herein, the term "substantially" refers to a great extent or degree. For example, "substantially all" typically refers to at least about 90%, frequently at least about 95%, often at least 99%, and more often at least about 99.9%.

"Dietary intolerance" and "food intolerance" are used interchangeably herein to refer to food sensitivity that occurs when a person has difficulty digesting a particular food and has an unpleasant physical reaction to them. It can lead to symptoms such as intestinal gas, bloating, spasm, cramping, abdominal pain, nausea, vomiting and diarrhea. Food intolerances involve the digestive system rather than the immune system, which is responsible for food allergy. Some food intolerance is caused by the lack or inadequacy of a particular digestive enzyme. Certain foods, particularly certain carbohydrates, can be frequent sources of food intolerance.

Malabsorption is a disorder that occurs when a person is unable to absorb nutrients from his or her diet, such as carbohydrates, fats, minerals, proteins, or vitamins, which can lead to nutrient deficiencies. Malabsorption may be global, with impaired absorption of almost all nutrients, or partial, with malabsorption of only specific nutrients. Causes of malabsorption include damage to the intestine from infection, inflammation, trauma, and surgery as well as specific diseases such as celiac disease, Crohn's disease, chronic pancreatitis, and cystic fibrosis.

"Effective amount", as used herein, refers to the amount of a compound or other substance that is sufficient in the presence of the remaining components to effect the desired result, such as reduction in a metabolite by at least about 50%, usually at least about 70%, typically at least about 90%, frequently at least about 95% and most often, at least about 99%. In other aspects of the invention, an "effective amount" of a biotherapeutic can refer to that concentration of the biotherapeutic that is sufficient in the presence of the remaining components to effect the desired result. The effective amount of a biotherapeutic or other substance is readily determined by one of ordinary skill in the art.

"Adaptive evolution" as used herein, refers a process of heritably changing a cell or population of cells by exposing the cell(s) to selective pressure and supporting survival of those that adapt to the pressure condition, without using artificial genetic engineering. Adaptive evolution is effected by naturally occurring mechanisms rather than by direct physical manipulation of the genome.

"Adaptively evolved microorganism" refers to an organism that has been heritably changed by a process of adaptive evolution.

"Selective pressure" and "selection pressure" are used interchangeably herein to refers to a condition under which organisms with certain phenotypes have either a survival benefit or disadvantage. For example, pressure to utilize a particular nutrient or substrate (a "pressure selection agent"), such as galactose, can be applied by including a physiologically significant amount of galactose in growth media with the result that those best able to utilize the galactose will preferentially survive.

A "genetically modified organism" or "GMO" is any organism whose genetic material has been altered using genetic engineering techniques, such as recombinant DNA, site-directed mutagenesis, gene transfer, and CRISPR. Genetic engineering excludes methods and processes that occur naturally.

"Microbiota," as used herein, refers to the ecological community of commensal, symbiotic and pathogenic microorganisms found in and on all multicellular organisms studied to date from plants to animals. A microbiota includes bacteria, archaea, protists, fungi and viruses. A microbiota can include all the microorganisms in and on a host, or can refer specifically to those populating a specific niche, such as the gut (i.e., gastrointestinal or digestive tract including the esophagus, stomach, small and large intestines), skin, mouth, reproductive tract or the like.

The term "microbiome" describes the collective genomes of a microbiota.

The present invention is based on the observation that microorganisms populating the gut ("gut microbiota") can complement defective host metabolism and/or remove intolerable dietary substances by acting directly in the human digestive tract and thereby contribute various functions to a symbiotic relationship with a human host including metabolism of carbohydrates.

Organisms such as Lactobacilli are the most common microorganisms in the human GI tract and have been widely used as delivery systems in the form of live biotherapeutics either as colonizers and/or delivery expression systems for therapeutic molecules. Yeasts represent another group of organisms that have been exploited as live biotherapeutic products given their generally recognized as safe (GRAS) status as well as their potential to restore gut function after long term antibiotic therapy. The present invention provides a live biotherapeutic approach to significantly minimize one or more symptoms related to fructose exposure.

The present invention provides a novel approach to treatment of carbohydrate consumption-related disorders, particularly as it relates to gastrointestinal pathologies and genetic-based systemic pathologies. This novel approach detoxifies carbohydrate (e.g., galactose, fructose) in the gut by the use of non-pathogenic microorganisms that minimize build-up of the carbohydrate and mitigate one or more of the symptoms and complications associated with elevated concentrations of the carbohydrate.

The present invention provides compositions and methods for the management of certain metabolic diseases, particularly diseases caused by deficient carbohydrate metabolism, such as galactosemia and fructosemia. The invention also provides methods for producing microorganisms (e.g., yeast and bacterial strains) that are effective at complementing deficient carbohydrate metabolism, thereby permitting treatment or reduction in symptoms and/or effects of disorders caused by deficient carbohydrate metabolism.

Also provided are tools for management of galactosemia, fructosemia and other metabolic diseases that develop a microbiota highly effective at complementing metabolic deficiencies by converting potentially toxic substances present in or derived from food to non-toxic and/or beneficial substances. In the case of galactosemia, the invention provides microorganisms that can replace a host' (e.g. human patients) deficient metabolism of galactose with organisms that are highly effective at degrading galactose present in the gut that originates from food, or directly in the food prior to consumption. To achieve these goals the invention provides microorganisms, particularly yeasts, that are viable and metabolically active for degrading galactose in the gut prior to its uptake into the blood stream by transporters located in the small intestine.

Similarly, in the case of fructose intolerance, malabsorption or metabolic disease, the invention provides microorganisms, which can replace deficient metabolism of fructose with organisms that are highly effective at degrading fructose present in the gut that originates from food, or directly in the food prior to consumption.

Also, considering the digestive transit kinetic, in certain embodiments, galactose-degrading and other yeast strains of the invention can act upon target molecules (e.g. certain carbohydrates) within a relatively short period of time in the gut before potential washout. Gastric emptying lasts an average of 1 h (Maurer et al., "The SNMMI and EANM Practice Guideline for Small-Bowel and Colon Transit 1.0." J Nuclear Med 54:2004-13 (2013)), whereas small intestine and colonic transit times are carried out for an average of 1 to 6 h and 72 h, respectively (Read et al., "Simultaneous measurement of gastric emptying, small bowel residence and colonic filling of a solid meal by the use of the gamma camera." Gut 27:300-8 (1986)). Moreover, formulations known in the art, such as enteric coatings, could further improve the recovery of viable yeast cells.

Advantageously, microorganism such as yeast and certain bacteria, can colonize and become a stable component of the gut microbiota. In certain aspects, inventive yeast strains and other microorganisms of the invention, have the ability to colonize the gastrointestinal tract of a human and to degrade galactose before its uptake into the blood stream. In such aspects of the invention, an alternative route of administration, e.g. via a nasogatric or orogastric tube, enema, or endoscopic administration may be suitable for populating the intestines. In other aspects, the microorganisms are stable through transit of the gastrointestinal tract, and can colonize the gut when administered orally. Thus, the biotherapeutic microorganisms of the invention can be long-acting, and in some cases may be a persistent or, in the absence of interventions that reduce or eliminate such microorganisms (e.g., antibiotic treatment) an ongoing and permanent treatment for dietary intolerance, malabsorption and/or metabolic disease. The persistence of microorganism colonization of the gut contrasts with therapeutic use of isolated dietary enzymes, such as lactase, which are unstable, degraded when passing through the digestive tract must be administered with each consumption of offending or intolerable food. In some embodiments, an effective dose of a biotherapeutic of the invention can be delivered by once, once-daily, once-weekly, once-monthly or as needed dosing.

Although dietary galactose restrictions are life-saving for infants, a strict dietary treatment does not appear to prevent all adult patients from developing complications of galactosemia. The cause of the complications has been explained by an endogenous production of galactose, amounting to 1 gram per day in adults. Berry et al., "Endogenous synthesis of galactose in normal men and patients with hereditary galactosaemia." Lancet 346:1073-74 (1995); Bosch "Classic galactosemia: Dietary dilemmas." J Inherit Metab Dis 34:257-60(2010)). Despite this observation, galactose reduction continues to be the mainstay of therapy with diet recommendations varying from very strict excluding milk together with certain fruits and vegetables to more liberal excluding dairy products only. Also, even if new modes of treatment are identified such as inhibitor agents of the defective galactose metabolic enzymes, diet restriction will likely remain the basis of galactosemia therapy because experts consider that it is still judicious to restrict galactose intake to manage its toxicity in adults. In this context, a yeast-based approach would permit broader diet flexibility. In addition, a yeast-based approach may alleviate some of the gastrointestinal symptoms associated with galactosemia (Shaw et al., "Gastrointestinal Health in Classic Galactosemia." JIMD Rep 33:27-32 (2016)), as the diet would be less restrictive and thus supportive of a more diverse microbiome with potentially positive outcome.

The present invention represents the first yeast-based approach to manage galactosemia that can significantly reduce galactose concentrations. Thus, in one embodiment, the invention provides an adaptively evolved yeast strain and methods for using the strain to degrade galactose in foods to safe levels that permit access to a simple and palatable diet.

The gut microbiota includes a large number of microorganisms, which may include bacteria, archaea, protists, fungi and viruses and/or viruses. Any of these are potentially suitable for use in adaptive evolution strategies of the invention. However, yeast are particularly attractive therapeutic agents for minimizing toxicity associated with high levels of galactose for a number of reasons. Yeast are natural components of the microbiome (Nash et al., "The gut mycobiome of the Human Microbiome Project healthy cohort." Microbiome 5:153 (2017)), that can express a galactose metabolic pathway similar to that found in humans. Sellick et al., "Chapter 3 Galactose Metabolism in Yeast—Structure and Regulation of the Leloir Pathway Enzymes and the Genes Encoding Them" Int Rev Cell Mol Biol 269:111-50 (2008). From a practical standpoint, certain yeast have the advantage over other microorganisms of a GRAS status (e.g. Generally Recognized As Safe) with cultures that can easily be established from a single, homogenous colony, just like bacteria, but devoid of DNA sequences that could potentially promote gene transfer to other gut microorganisms. Yeast has also been found to be able to establish itself in the gastrointestinal tract in areas where bacteria may not thrive. Czerucka et al., "Yeast as probiotics—*Saccharomyces boulardii*." Alimentary Pharmacol Therapeutics, 26:767-78 (2007). Moreover, yeast has already been used in human medicine, for instance for the treatment of antibiotic-associated diarrhea. Kelesidis et al., Therapeutic Adv Gastroenterol 5:111-25 (2011); Tung et al., "Prevention of *Clostridium difficile* Infection with *Saccharomyces boulardii*: A Systematic Review." Can J Gastroenterol 23:817-21 (2009).

The present invention provides microorganisms, such as yeast, adaptively evolved and evaluated for reducing toxicity originating from food sources, particularly carbohydrates such as galactose and fructose. The present invention also provides methods for generating and selecting microorganisms (e.g. yeast strains) that preferentially or exclusively utilize galactose even in presence of other carbohydrates. In other aspects, the invention provides methods for generating and selecting microorganisms (e.g. yeast strains) that preferentially or exclusively utilize galactose even in presence of other carbohydrates.

Microorganisms suitable for use in the methods of the invention are generally non-pathogenic and frequently generally recognized as safe ("GRAS") when introduced into the gastrointestinal tract of a human, typically by oral consumption, but can be by any route, such via a nasogastric tube, an orogastric tube, an enema or an endoscope. In certain aspects, orally administered microorganisms can be directed to a particular region of the gastrointestinal tract, e.g. by enterically coating the microorganism.

Yeast contemplated for use in the methods of the invention include, but are not limited to: *Saccharomyces* species (spp.) such as *Brettanomyces* spp. such as *B. bruxellensis*; *S. cerevisiae, S. boulardii, S. fragilis, S. bayanus, S. beticus, S. eubayanus, S. fermentati, S. jurei, S. kudriavzevi, S. paradoxus, S. pastorianus*, and *S. uvarudm, S. cerevisiae* x *S. eubayanus* x *S. uvarum, S. eubayanus* x *S. uvarum*; *Saturnispora* spp. such as *S. zaruensis*; *Pichia (Scheffersomyces)* spp. such as *P. stipites, P. cecembensis*; *Schizosaccharomyces* spp. such as *S. cryophilus, S. japonicus, S. octosporus*, and *S. pombe*; *Saccharomycodes* spp. such as *S. ludwigii*; *Debaromyces* spp, such as *D. hansenii*; *Kazachstania* spp. such as K *unispora*; *Kluyveromyces* spp. such as *K marxianus*, K *wickerhamii*, *K lactis*, and *K. lodder, K. wickerhamii; K. dobzhanskii*; *Torulaspora* spp. such as *T. delbrueckii*; *Yarrowia* spp. such as *Y. lipolytica* and *Zygosaccharomyces* spp. such as *Z kombuchaensis. Kluyveromyces marxianus*; *Hanseniaspora* spp. such as *H. opuntiae, H. thailandica*, H *uvarum*; *Limtongozyma cylindracea Saccharomyces* sp.; *Metschnikowia* spp. such as *M. bicuspidate, M. chrysomelidarum, M. cibodasensis, M. colchici, M. gelsemii, M. gruessii, M. henanensis, M. kofuensis, M. maroccana, M. noctiluminum, M. peoriensis, M. rancensis, M. reukaufii, M. vanudenii, M. viticola, M. zobellii*; *Hanseniaspora* spp. such as *H. opuntiae, H. thailandica*, and *H. uvarum*.

Additional fungi that may be useful in certain aspects of the invention include: *Aspergillus* spp. such as *A. oryzae, A. sojae*, and *A. tamarii*; *Penicillium* spp. such as *P. camemberti* and *P. roqueforti*; *Rhizopus* spp. such as *R. oligosporus* and *R. oryzae*.

In certain embodiments of the invention, bacteria may be used instead of fungi. Such bacteria include, but are not limited to: *Lactobacillus* spp. such as *L. acidophillus, L. amylovorus, L. bulgaricus, L. brevis, L. casei, L. crispatus, L. curvatus*, cL. *Delbrueckii, L. fermentum, L. gallinarum, L. gasseri, L. helveticus, L. jensenii, L. johnsonii, L. kefiranofaciens, L. latis, L. parcasei, L. plantarum, L. reuteri, L. rhamnosus, L. salivarius*, and *L. sakei*; *Bifidobacteria* spp. such as *B. adolescentis, B. animalis, B. bifidum, B. breve, B. infantis, B. lactis*, and *B. longum*; *Bacillus* spp. such as *B. cereus, B. clausii, B. coagulans, B. infantis, B. pumilus, B. subtilis*, and *B. coagulans*; *Lactococcus* spp. such as *L. lactis*; *Enterococcus* spp., such as *E. durans* and *E. faecium*; *Eubacterium* spp. such as *E. faecium*; *Leuconostoc* spp. such as *L. citreum, L. cremoris, L. gasicomitatum, L. gelidum, L. kimchi* and *L. mesenteroides*; *Oenococcus* spp. such as *O. oeni*; *Pedicoccus* spp. such as *P. acidilactici, P. pediococcus*, and *P. pentosaceus*; *Propionibacterium* spp. such as *P. acidipropionici, P. freudenreichii, P. jenseniil*, and *P. shermanii*; *Sporolactobacillus* spp. such as *S. inulinus*; *Streptococcus* spp. such as *S. thermophilus*; *Tetragenococcus* spp. such as *S. halophilus*; and *Weissella* spp. such as *W. confuse, W. kimcii* and *W. koreensis*.

The present invention provides method for adaptively evolving a microorganism, including the steps of providing a microorganism; growing the microorganism under an adaptive condition, wherein the organism adapts to the adaptive condition; and confirming adaptation of the microorganism, thereby adaptively evolving the microorganism. Typically, there is a clonal population of cells of the microorganism that can be isolated by plating cells of the microorganism on an agar plate under conditions that yields single colonies of the cells; growing the plated cells on the agar plate; and picking a single colony of the cells from the plated agar plate, thereby isolating the clonal population of cells.

Other methods of isolating a clonal population of cells, such as limiting dilution, are known in the art.

Growing the microorganism under an adaptive condition can, for example include inoculating a culture medium comprising the adaptive condition with the isolated microorganism; growing the microorganism in the culture medium to prepare an actively growing adaptive culture; diluting the actively growing adaptive culture with fresh medium comprising the adaptive condition; and repeating the growth and dilution steps from 1 to 100 time. The growth and dilution steps can be repeated at any suitable interval that maintains the culture in a rapidly growing state based on time, such as weekly, twice weekly, every second day, daily, twice daily or every 8 hours or based on OD. In certain embodiments, the serial dilution process is repeated every 12-24 hours, such as every 16 hours. The serial dilution process can be repeated as many times as necessary to obtain adaptation of the microorganism. In certain aspects, the serial dilution process is repeated 7-10 times, in other aspects, it is repeated 10-25 times or more.

Typically, the adaptation results in a change in growth efficiency of the microorganism and confirming adaptation of the microorganism is based on detecting the change in growth efficiency, such as by measuring generation time, specific growth rate, or doubling time and observing a change in at least one of these parameters. In certain aspects, cell growth is monitored prior to each serial dilution, e.g. by measuring the optical density of the culture, which is a function of cell density.

The frequency of serial dilution will depend on the generation time of the organism under the adaptive condition, and may require at least 20 cell generations, at least 50 cell generations, at least 75 cell generations to obtain a desired change The adaptation can, for example, result in the increase in synthesis of a substance (e.g., an enzyme, vitamin or co-factor) or it can be an increase in metabolism of a food or nutrient, such as the ability of the microorganism to use a carbon source (e.g., a specific carbohydrate).

In specific embodiments of the invention, the microorganism adaptively evolves to utilize galactose as a carbon source and the adaptive condition includes the presence of galactose, and can also include presence of glucose.

In other embodiments of the invention, the microorganism adaptively evolves to utilize fructose as a carbon source and the adaptive condition includes the presence of fructose, and can also include presence of glucose.

The invention also provides adaptively evolved microorganism prepared according to the methods described herein. In one embodiment, adaptively evolved microorganism metabolizes galactose, typically in the presence of glucose. In one aspect, the invention provides adaptively evolved microorganisms derived from *Saccharomyces cerevisiae*. Advantageously, adaptively evolved microorganisms of the invention degrade galactose in present in food, such as milk.

The conditions encountered in the gastrointestinal tract, including the gastric fluid environment, intestinal fluid environment, more particularly the gastric fluid environment followed by an intestinal fluid environment, can be hostile to microbiological growth.

In certain aspects of the invention, the adaptively evolved microorganisms are capable of colonizing the gastrointestinal tract thereby providing long-term galactose metabolism. In certain embodiments of the invention, at least 10, 20, 30 or 40% of the cells will demonstrate properties indicative of the ability to colonize the gastrointestinal tract. The methods can allow the subject to consume galactose containing or galactose producing (upon digestion) food without low absorption of galactose from the food into the bloodstream.

In certain aspects the adaptively evolved microorganism is administered prior to consuming food, such as with meals three times per day. The effective amount of the adaptively evolved microorganism reduces the amount of galactose by at least 50% and/or eliminates absorption of at least 90% of the galactose in the consumed food. In embodiments of the invention where the microorganism colonizes the gastrointestinal tract, long-term galactose reduction or elimination from food-based sources may be achieved.

Also provided by the invention are compositions containing one or more galactose metabolizing enzyme from the adaptively evolved microorganisms described herein. Such compositions can be pharmaceutical composition suitable for administration to a subject and/or they can be suitable for addition to food. Effective amounts of either composition reduce the amount of galactose in food either prior to or after consumption of the food.

EXAMPLES

Deposit of Microorganisms

Applicant has made a deposit with Agricultural Research Culture Collection (NRRL), International Depositary Authority of the following strains on Mar. 11, 2020, under the terms of the Budapest Treaty: *Saccharomyces cerevisiae* clone Y_C202_1 Accession No. NRRL Y-67930; *Saccharomyces cerevisiae* clone Y_C201_1 Accession No. NRRL Y-67931; *Kluyveromyces marxianus* clone K_219 Accession No. NRRL Y-67932; *Pichia kudriavzevii* clone G1_1A Accession No. NRRL Y-67933; *Saccharomyces cerevisiae* clone G2_1A Accession No. NRRL Y-67934; *Saccharomyces uvarum* clone G3_1A Accession No. NRRL Y-67935; and *Metschnikowia reukaufii* clone G4_1A Accession No. NRRL Y-67936.

Example 1. Identification of Yeast Strains Capable of Degrading Galactose

A primary goal of the present invention was to develop yeast strains highly effective at metabolizing galactose. However, galactose-metabolizing yeasts are uncommon; yeasts typically prefer glucose, a carbohydrate source known to strongly suppress the expression of genes needed to metabolize other carbohydrates such as galactose (See Escalante-Chong et al., "Galactose metabolic genes in yeast respond to a ratio of galactose and glucose." Proc Nat'l Acad Sci, USA 112:1636-41 (2015)). Wild type yeast strains may thus be prevented from utilizing any carbohydrates when glucose is present. Even if a yeast does have the capability to use other carbohydrate sources, it may occur late in the growth process, only after glucose has been completely depleted. Therefore, a particular type of galactose-metabolizing yeast was developed that degrades galactose in the presence of glucose. The present invention provides methods for adaptively evolving yeast according to this process.

To assess the ability of a yeast strain to degrade galactose, its growth was evaluated on media containing galactose in presence or absence of glucose. The following strains were tested: the commercially available strains *Saccharomyces cerevisiae* (N) (Natureland, *Saccharomyces boulardii* (SB) (Jarrow, Santa Fe Springs, CA), and *Saccharomyces boulardii* (B) (Biocodex, Redwood City, CA). Additional strains included in the screening were isolated from food containing large amounts of galactose such as dairy products and legumes stored at room temperature for over two weeks.

Cultures of various strains were initiated from a single colony on agar plates or from glycerol stocks, and grown in liquid YP medium (1% yeast extract, 2% peptone; Teknova) by incubation at 30° C. with agitation at 125 rpm (Murakami & Kaeberlein "Quantifying Yeast Chronological Life Span by Outgrowth of Aged Cells." J Visual Exp (27) (2009)). Overnight yeast cultures initiated in duplicate in liquid YP medium were used as pre-cultures to initiate growth efficiency experiments in liquid CM (Synthetic Complete Minimal Medium, 0.5% Ammonium Sulfate, Teknova) containing 2% galactose alone as the sole carbon source, 2% glucose alone as the sole carbon source, or galactose and glucose. Culture growth of cultures set at 30° C. under static conditions was monitored over time by measuring optical density (OD) at 600 nm ($OD_{600}$) using a spectrophotometer.

Growth—was evaluated for several strains. As illustrated in Table 1, one of the evolved clone exhibited the lowest doubling time, which remained at the same level independently of the carbohydrate source and growth conditions.

TABLE 1

Doubling Time of Yeast Strains under Static Growth Conditions in Media Containing Galactose alone, Glucose alone, and Galactose and Glucose.

| Strains | Galactose | | Galactose + Glucose | | Glucose | |
| --- | --- | --- | --- | --- | --- | --- |
| | Avg. (h) | SD | Avg. (h) | SD | Avg. (h) | SD |
| Y1_Parent | 4.57 | 0.03 | 4.43 | 0.05 | 4.40 | 0.01 |
| Evolved Clone | 4.05 | 0.02 | 4.17 | 0.08 | 4.21 | 0.02 |
| Strain N | 6.05 | 0.03 | 4.46 | 0.02 | 4.23 | 0.01 |
| Strain SB | 7.79 | 0.06 | 4.68 | 0.00 | 4.75 | 0.03 |
| Strain B | 8.85 | 0.02 | 4.96 | 0.02 | 4.63 | 0.01 |

Each data point represents the averages (Avg.) and standard deviation (SD) of quadruplicate values obtained for two independent cultures per strain.

Example 2: Adaptive Evolution Results in Superior Yeast Strains

Adaptive evolution—was applied to yeast strains, a method that can increase traits of a given strain owing to random mutations in the genome. Clones derived from parental strains that offer a phenotypic advantage are naturally selected when grown under selective pressure. Yeast can be subjected to adaptive evolution with changes that can be observed in a short time period because yeast grows rapidly as single cells in simple media, with the entire life cycle completed in culture similarly to bacteria.

Adaptive evolution was carried out by daily serial dilution of independent clonal populations of parental strains (See Çakar et al., "Evolutionary engineering of *Saccharomyces cerevisiae* for improved industrially important properties." FEMS Yeast Res 12:171-82 (2011)). Parallel cultures were independently grown at 30° C. under agitation at 125 rpm in 15 mL CM medium in 50 mL vented tubes or 3 mL in 14 mL culture tubes supplemented with 2% galactose as a pressure selection agent for about 16 to 30 hours before transferring the cultures to fresh medium at a 1:30 dilution. The procedure of serial dilution was repeated until a change in growth was detected by $OD_{600}$.

A volume of 100 µL of a 1:1,000 dilution of the last daily serial dilution of the culture with the greatest OD was plated on YP-galactose agar medium (Teknova) and incubated at 30° C. Isolated, adaptively evolved clones were randomly selected from the plate to start duplicate cultures grown at 30° C. under agitation at 125 rpm in 3 mL CM medium supplemented with 2% galactose alone or 2% galactose and glucose.

To assess the yeast strains' and clones' ability to degrade galactose, the concentration of galactose in spent medium was determined using the colorimetric Galactose Assay Kit (Cat. No. EGAL-100; BioAssay Systems, Hayward, CA). All reactions were performed in 96-well microplates and the absorbance was read at 570 nm using volumes and concentrations recommended by the kit. The samples and standards were mixed with the enzyme and the substrate, which reacts with galactose to produce hydrogen peroxide. Hydrogen peroxide reacts with the colorless substrate, which, in presence of horseradish peroxidase (HRP), produces a pink-colored product with an intensity proportional to galactose concentration. Sample concentrations were determined by comparison to a standard curve generated with known quantities of galactose.

Utilization and degradation of galactose was assessed by measuring the consumption of galactose in spent culture medium. Amongst the adaptively evolved strains generated by serial dilution from two parent strains, some clones exhibited a greater level of reduction of galactose concentration compared to the parent strains. Table 2, below, lists the percentage of galactose reduction in spent culture medium for the adaptively evolved strains and the parent strains when cultured for 8 hours at 30° C. in CM medium supplemented with 2% galactose alone or with galactose and glucose.

This data set illustrates that the adaptively evolved clones were able to significantly degrade galactose. More importantly, some clones were also able to utilize galactose even in presence of glucose, demonstrating that they were not affected by glucose catabolite repression. Strain Y1_2 exhibited a reduction greater than 94.4% of galactose concentration compared to less than 1% reduction for the parental strain Y1 in spent medium at the 8 hour time point. This difference is statistically significant, confirming that adaptive evolution produced a more efficient strain.

TABLE 2

Utilization of Galactose of Adaptively Evolved Clones (Y1_1 to Y1_7; Y2_1 to Y2_7) Compared to the Parent Clones Y1 and Y2.

| Clones No: | Y1_1 | Y1_2 | Y1_3 | Y1_4 | Y1_5 | Y1_6 | Y1_7 | Y1_Parent |
|---|---|---|---|---|---|---|---|---|
| Galactose | 69.4% | 61.6% | 83.6% | 60.2% | 73.2% | 55.7% | 64.1% | 32.1% |
| Gal + Glu | 83.2% | 94.4% | 85.0% | 70.7% | 61.9% | 32.3% | 72.9% | 0.1% |

| Clones No.: | Y2_1 | Y2_2 | Y2_3 | Y2_4 | Y2_5 | Y2_6 | Y2_7 | Y2_Parent |
|---|---|---|---|---|---|---|---|---|
| Galactose | 32.4% | 42.5% | 43.2% | 51.9% | 45.9% | 49.3% | 50.7% | 27.3% |
| Gal + Glu | 31.9% | 29.9% | 32.9% | 38.7% | 46.0% | 58.2% | 56.9% | 34.4% |

Values represent averages of percent reduction of galactose concentration from two independent cultures grown for 8 hours at 30° C.

Example 3: Isolation and Identification of Galactose-Degrading Strains

This study was focused on isolating yeast strains that would have the ability to degrade galactose. Yeasts were isolated from galactose-rich food samples such as dairy products and legumes. Various species were isolated by cultivating the samples in culture medium containing galactose at room temperature for a period of time of at least 2 days. The isolates were then subjected to adaptive evolution eventually followed by UV treatment to generate clones with superior galactose-detoxification performance. Taxonomy was assigned to isolates by a molecular approach based on targeted sequencing of Internal Transcribed Spacers (ITS).

Strains were isolated mainly from two sources: legumes (chickpeas, beans) and dairy product (kefir). For legumes, the seeds were collected into sterile flasks. For milk product, an aliquot of home-made kefir was utilized as inoculum. After cultivation for approximately 2 weeks at laboratory temperature with an agitation of 125 rpm in liquid minimal medium supplemented with 2% galactose (Teknova) and 50 ug/mL chloramphenicol (Teknova, Cat C0380), cultures were serially diluted and seeded again in liquid medium with selection and incubated at 30° C. with agitation of 125 rpm. This cycle was performed at least 3 times until plating serially diluted cultures on YP-2% galactose agar plates. Single colonies obtained after incubation at 30° C. for 2-5 days were sequentially streaked multiple times to obtain pure isolates.

For taxonomy assignment, the targeted metagenomic sequencing method was employed. Briefly, the isolates were processed for DNA extraction using the ZymoBIOMICS®-96 MagBead DNA Kit and the DNA samples were prepared for targeted sequencing using targeted Internal Transcribed Spacers primer sets (ITS2, Zymo Research, Irvine, CA). The final library was sequenced on Illumina® MiSeq™. Taxonomy analyses were performed on publicly available sequences using the BLAST program under default settings (www-dot-ncbi-dot-nlm-dot-nih-dot-gov/BLAST).

The ITS sequences obtained from pool cultures and from isolate cultures were analyzed to identify isolate phylogeny. Table 3 reports the outcome of this analysis ("Hits") based on the homology of ITS sequences amplified from pool cultures and purified isolate cultures with publicly available sequences. The Table lists the species exhibiting the greatest score and 100% sequence identity with ITS sequences obtained from this study.

TABLE 3

Blast Results of Sequences Obtained after Amplification of Internal Transcribed Spacers (ITS) from Pool Cultures and from Isolate Cultures.

| Source | Hits |
|---|---|
| List of potential assignment for pool isolated from legume | *Saccharomyces* sp, *Saccharomyces uvarum*, *Saccharomyces cerevisiae*, *Saccharomyces cerevisiae* × *Saccharomyces eubayanus* × *Saccharomyces uvarum*, *Saccharomyces bayanus*, *Saccharomyces paradoxus*, *Saccharomyces jurei*, *Saccharomyces* sp. 'boulardii', *Saccharomyces eubayanus*, *Saccharomyces kudriavzevii*, *Pichia* sp. |
| Taxonomic assignment as per Blast search for isolate Yi derived from legume pool | *Saccharomyces cerevisiae* |
| List of potential assignment for pool isolated from dairy product | *Saccharomyces* sp., *Saccharomyces uvarum*, *Saccharomyces cerevisiae*, *Saccharomyces cerevisiae*, *Saccharomyces eubayanus* × *Saccharomyces uvarum*, *Saccharomyces bayanus*, *Saccharomyces paradoxus*, *Saccharomyces jurei*, *Saccharomyces euhayanus*, *Saccharomyces kudriavzevi*, *Pichia* sp., *Kluyveromyces marxianus*, *Kluyveromyces lactis*, *Kluyveromyces dobzhanskii*, *Kluyveromyces wickerhamii*, *Kluyveromyces* sp., *Kazachstania unispora* |
| Taxonomic assignment as per Blast search for isolate Ki derived from legume pool | *Saccharomyces* sp. |

Adaptive evolution was carried out on the isolates by daily serial dilution conducted for at least 30 cycles, corresponding to approximately 180 generations of the parental strain Yi isolated from legumes. Two clones identified as lead clones, clone Y-C201 and clone Y-C202 were subjected to UV treatment as follows. A volume of 100 µL of a 1:1,000 dilution from an overnight 3 mL-culture grown at 30° C. under agitation at 125 rpm in CM medium supplemented with 2% galactose was plated on YP-2% galactose agar medium. The petri dishes were exposed to UV rays (235 nm) in the biosafety cabinet at a distance of 20 cm. The plates were then incubated in the dark for at least 3 days at 30° C. Isolated clones were randomly selected from the UV-treated plates to start duplicate cultures. After multiple rounds of screening tests evaluating growth and galactose consumption in presence or absence of glucose, three lead clones were selected: clone Y-C201-1 deriving from clone Y-C201 and clones Y-C202-1 and Y-C202-2 deriving from Y-C202.

Example 4: Degradation of Galactose in Food and Beverages

As part of evaluating the feasibility of a yeast-based approach as a treatment to mitigate the effects of elevated concentrations of galactose in foods and beverages, several evolved clones were tested for their capability of degrading galactose when present in food. Milk was tested because it represents the most challenging food for galactosemia patients considering its high level of galactose (2-4 g per 100 mL of milk). Food spiked with galactose was tested in parallel.

For this study, three evolved yeast strains obtained by adaptive evolution followed by UV treatment, Clone Y-C201-1, Clone Y-C202-1, and Clone Y-C202-2, one evolved yeast strain obtained by adaptive evolution, Clone Y-C202, as well as the initial parent strain Yi were compared for their galactose consumption activity. Cultures were initiated from a single colony on agar plates and grown in 15 mL of liquid YP medium (1% yeast extract, 2% peptone; Teknova, Hollister, CA) in a 50-mL mini-bioreactor by incubation at 30° C. with an agitation of 225 rpm supplemented with 2% galactose (Teknova). Strain *Saccharomyces boulardii* (SB) was prepared similarly to the evolved clones except that it was grown in YP medium supplemented with 2% glucose.

The testing of galactose consumption was started with yeast cells obtained from a culture volume containing 1.0× $10^9$ Colony Forming Units (CFU) pelleted by centrifugation at 1000 rpm (Sorval, RT7) for 10 min at room temperature. Cell pellets were resuspended either in 1.0 mL of milk already pre-treated with lactase (LACTAID milk where lactose is transformed into galactose and glucose) or in 1 mL rodent diet (Teklad, Envigo) spiked with a solution of 5% galactose or a solution of 5% galactose+1% glucose. All the reactions were incubated at 37° C. Aliquots of the reactions were taken at multiple time points and stored at −20° C. until galactose concentration determination.

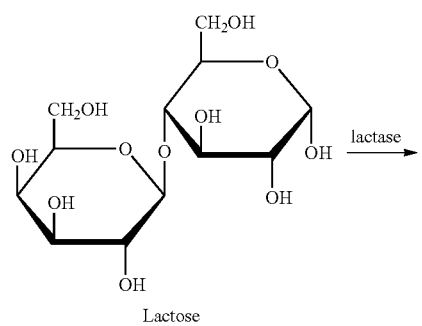

Lactose

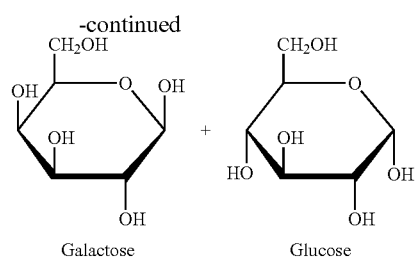

Galactose       Glucose

Conversion of Lactose to Galactose and Glucose

As shown in Table 4, Table 5, and Table 6, the evolved clones were able to rapidly decrease galactose concentration present in milk and in spiked-diet whereas strain SB did not decrease the galactose concentration. More importantly, the evolved clones were also able to utilize galactose even in presence of glucose, demonstrating that there were not affected by glucose catabolite repression.

TABLE 4

Galactose concentration (mM) in milk after exposure to strains for a period of 1 hour

| Time point (hr) | Y-C201-1 | Y-C202 | Y-C202-1 | Y-C202-2 | Yi | SB | Milk |
|---|---|---|---|---|---|---|---|
| 0.1 | 125.07 | 131.25 | 135.96 | 135.12 | 162.10 | 180.24 | 171.24 |
| 1 | 16.50 | 11.23 | 34.68 | 40.75 | 156.51 | 172.22 | 187.96 |

TABLE 5

Galactose concentration (mM) in diet spiked with 5% galactose and 1% glucose after exposure to strains for a period of 0.1 to 3 hours

| Time point (hr) | Y-C201-1 | Y-C202 | Y-C202-1 | Y-C202-2 | Yi | SB | Diet 5% Galactose 1% Glucose |
|---|---|---|---|---|---|---|---|
| 0.1 | 286.89 | 269.65 | 262.67 | 284.94 | 314.39 | 305.63 | 324.16 |
| 1 | 167.19 | 126.95 | 132.29 | 137.21 | 327.20 | 312.06 | 334.32 |
| 2 | 4.18 | 2.54 | 2.47 | 2.33 | 318.41 | 308.60 | 327.24 |
| 3 | 1.95 | 2.85 | 2.85 | 3.48 | 287.49 | 310.62 | 307.31 |

TABLE 6

Galactose concentration (mM) in diet spiked with 5% galactose after exposure to yeast strains for a period of 0.1 to 3 hours

| Time point (hr) | Y-C201-1 | Y-C202 | Y-C202-1 | Y-C202-2 | Yi | SB | Diet 5% Galactose |
|---|---|---|---|---|---|---|---|
| 0 | 284.17 | 268.96 | 224.74 | 244.88 | 232.57 | 304.52 | 313.17 |
| 1 | 169.98 | 142.31 | 129.43 | 123.04 | 176.86 | 301.41 | 322.39 |
| 2 | 3.83 | 2.37 | 2.30 | 2.12 | 169.46 | 306.93 | 315.51 |
| 3 | 1.81 | 2.71 | 2.78 | 3.20 | 165.41 | 306.26 | 332.58 |

Example 5: Tolerance to Gastrointestinal Conditions

The most convenient way to deliver a yeast-based therapeutic is orally. During transit through the gastrointestinal tract, an orally delivered agent will be confronted with a variety of simultaneous or sequential adverse conditions, such as the internal body temperature, gastric fluid with acidic pH, and pancreatic fluid with alkaline fluid. A series of in vitro experiments were conducted to assess the potential for survival of the evolved clones when subjected to gastrointestinal conditions.

Yeast cells were subjected to simulated gastric fluid (SGF) supplemented with 1 mg/mL of pepsin and simulated intestinal fluid (SIF) supplemented with 1 mg/mL of pancreatin to evaluate their tolerance to gastrointestinal conditions. Zhou et al. "Statistical investigation of simulated fed intestinal media composition on the equilibrium solubility of oral drugs." Eur J Pharm Sci 99:95-104 (2017). Overnight yeast cultures grown in liquid YP medium supplemented with 2% galactose were harvested by centrifugation for 10 min at 1000 rpm at room temperature. To test for survival in gastric fluid, pellets were re-suspended in 1 mL SGF (Cat No. 7108.16; RICCA Chemical Company, Arlington, Texas) supplemented with pepsin from porcine gastric mucosa with an activity of 8.60 European Units/mg (Cat No. 41707-1000; ACROS Organics, Geel, Belgium). The pH was measured (pH~2) and the reactions were maintained at 37° C. for 240 min. Cells were also tested for survivability in SGF added to dry diet pellet (5 mL of SGF added to 1 g diet, Teklad Diet). To test for survival in intestinal fluid, cells were centrifuged for 10 min at 1000 rpm at room temperature and re-suspended in 1 mL SIF (RICCA Chemical Company, Cat No. 7109.16, pH 6.7-6.9 supplemented with 1 mg/mL of pancreatin from porcine pancreas (Sigma, Cat No. P3292). All reactions were maintained at 37° C. for 240 min. Yeast cells were counted before and after intestinal challenges with Simulated Gastric Fluid (SGF) and Simulated Intestinal Fluid (SIF). The survival rate was estimated by evaluating the ratio between cell counts of yeast preparations subjected to the simulated fluid challenge over time vs. the same preparations at time zero. Viable cell counts were determined using a hemocytometer and Trypan blue staining.

As shown in Table 7, the gastric environment had an impact on strain survival. Simulated gastric triggered a cell count decrease of approximately 5% within 20 min but there were no major changes of cell counts when the cells were exposed SGF resuspended in dry diet. Interestingly, the simulated intestinal fluid did not appear to have a significant effect on cells

TABLE 7

Survivability Time Course (%) of Evolved Clone Y_C202_1 in Gastrointestinal Conditions after Exposure to Simulated Fluids over a period of 0 to 240 min

| Time point (min) | SGF | SIF | PBS | SGF, Diet |
|---|---|---|---|---|
| 0 | 100.0 | 100.0 | 100.0 | 96.3 |
| 20 | 95.9 | 100.0 | 100.0 | 95.0 |
| 40 | 20.8 | 100.0 | 100.0 | 98.2 |
| 60 | 0.0 | 100.0 | 100.0 | 92.7 |
| 120 | ND | 100.0 | 100.0 | 94.6 |
| 240 | ND | 100.0 | 100.0 | 95.2 |

SGF—Simulated Gastric Fluid; SIF—Simulated Intestinal Fluid, SGF, Diet—Simulated Gastric Fluid with Diet; ND—Not Determined.

Example 6: Mitigation of Galactose Accumulation in Serum after a Single Oral Administration of the Evolved Clone The objective of this study was to assess the ability of the test article to detoxify galactose in vivo. To that end, galactose concentration was investigated in serum and urine after a single bolus oral administration to animals of 10% galactose with and without the test article.

Animal care and procedures were approved by the Institutional Animal Care and Use Committee and were followed in accordance to the standards for animal husbandry and care of the U.S. Department of Agriculture's (USDA) Animal Welfare Act. Veterinary care was available throughout the course of the study and animals were examined by the veterinary staff as warranted.

Fifteen-week-old male Sprague-Dawley rats weighing between 350 and 400 g were acquired from Envigo with a catheter surgically implanted in the jugular vein. Animals were housed individually in polycarbonate cages containing animal bedding during the acclimation period lasting 7 days. Environmental controls were maintained at 18 to 23° C. with humidity of 30% to 70% with automatic lighting on a 12 h/12 h on/off cycle except as required for specimen collection and study conduct. Animals were fed an irradiated chow diet (Pico Lab, Lab Diet 5053) and were provided municipal tap water ad libitum. Animals were housed individually in metabolic cages following the single bolus dose until end of study. No concurrent medication was given.

The rats were randomly distributed into three groups, each consisting of three animals. Group I was administered with a solution of 10% (=555 mM) galactose; Group II was administered with the test article together with a solution of 10% galactose; and Group III was administered with the test article only. All animals were fasted for a period of 16 hour prior to dosing and all animals were administered a single bolus dose by oral gavage with a total volume of 10 mL/kg. The cell density of the test article was 2E+09 CFU/mL prepared from an overnight culture incubated at 30° C. in orbital shaker and grown in YP medium supplemented with 2% galactose. Blood samples (0.3 mL) were collected serially via catheterized jugular veins at 0, 0.5, 1, 1.5, 2, 4, 8, and 24-hour after dosing for analysis of galactose concentration in serum. Urine samples were collected at intervals from 0 to 4 hours, 4 hours to 8 hours, and 8 hours to 24 hours after the single bolus administration for analysis of galactose concentration. All samples were stored frozen until analysis. Galactose levels in urine and serum samples were determined using the EnzyChrom™ Galactose Assay Kit (BioAssay Systems, Hayward, CA) and analyzed in duplicate in a microplate reader (Molecular Devices).

As reported in Table 8, galactose concentration rose sharply to a concentration of 10.5 mM after administration of a single bolus dose of 10% galactose (555 mM) and reached its peak level in serum 60 min after administration by oral gavage. There was also a marked increase of galactose concentration in urine, approximately greater than 50% of the loaded dose (Table 9). Interestingly, for the group treated with the test article concurrently to galactose, the concentration of galactose in serum samples and urine samples were low and within the same range than the samples from the control group treated with the test article alone.

The data indicate that the strain administered to rats resulted in a potent reduction of galactose in serum and in urine. Thus, the strain appears to be effective at detoxifying galactose when delivered orally.

TABLE 8

Galactose concentrations (mM) in serum collected from animals
at 0, 0.5, 1, 1.5, 2, 4, 8, and 24-hour post administration
by oral gavage of 10% galactose, of the test article with
a solution of 10% galactose, and of the test article alone.

| Time Point (hr) | Group 1 10% Galactose | Group 2 Test Article + 10% Galactose | Group 3 Test Article |
| --- | --- | --- | --- |
| 0 | −0.52 | −0.52 | −0.56 |
| 0.5 | 9.69 | −0.02 | −0.54 |
| 1 | 10.49 | 0.15 | 0.00 |
| 1.5 | 4.26 | −0.31 | −0.42 |
| 2 | 2.19 | −0.51 | −0.49 |
| 4 | −0.52 | −0.06 | −0.56 |
| 8 | −0.38 | −0.50 | −0.52 |
| 24 | −0.39 | −0.35 | −0.41 |

Data points represent means of duplicate values obtained for 3 animals per group.

TABLE 9

Galactose concentrations (mM) in urine collected from animals
at period intervals of [0-4 hours], [4-8 hours],
and [8-24 hours] post administration by oral gavage
of 10% galactose and of the test article alone and with 10% galactose.

| Time Intervals | Group 1 10% Galactose | Group 2 Test Article + 10% Galactose | Group 3 Test Article |
| --- | --- | --- | --- |
| 0 to 4 hr | 112.64 | 6.89 | 0.039 |
| 4 to 8 hr | 28.82 | 0.06 | 0.19 |
| 8 to 24 hr | 1.86 | −0.02 | 0 |

Data points represent means of duplicate values obtained for 3 animals per group.

Example 7: Mitigation of Galactose Accumulation in Serum after Multiple Oral Administrations of the Evolved Clone The objective of this study was to test the ability of the test article to detoxify galactose when galactose is provided multiple times. To that end, four groups of three Sprague-Dawley male rats were dosed with PBS (with 12.5% galactose in drinking water), test article (with and without 12.5% galactose in drinking water), and test article concurrently with 12.5% galactose via three daily oral gavage administration for 10 Days. Galactose concentration in serum was determined serially over five separate time points.

Animal care and procedures were approved by the Institutional Animal Care and Use Committee and were followed in accordance to the standards for animal husbandry and care of the U.S. Department of Agriculture's (USDA) Animal Welfare Act. Veterinary care was available throughout the course of the study.

A total of 12 healthy adult male Wistar rats weighing between 110 to 130 g procured from Envigo (Livermore, CA) and maintained in the controlled conditions of 18 to 23° C. with humidity of 30% to 70% with automatic lighting on a 12 h/12 h on/off cycle except as required for specimen collection and study conduct. The rats were fed with standard pellet diet (Teklad 18% protein, Envigo) and water ad libitum throughout the study. The rats were divided into four groups of three animals each. For Group I, the rats were administered the test article alone. For Group II, the rats had access ad libitum to a solution of 10% galactose prepared with tap water and were administered a solution of PBS. For Group III, the rats were administered the test article and had access ad libitum to a solution of 10% galactose prepared with tap water. For Group IV, the rats were administered the test article together with a solution of 10% galactose.

The dose volume to administer was calculated based on the most recent recorded body weight. Formulated test article for group 1, group 3 and group 4 animals had a cell count averaging 1E+09 CFU/mL. Each group of animals received their respective treatment via oral gavage administration three times daily (10 mL/kg body weight) at 0 hour, 3 hours post $1^{st}$ daily dose, and 6 hours post $1^{st}$ daily dose starting on Day 0 over a period of 10 days. Drinking water for animals in groups 2 & 3 was replaced with water supplemented with 12.5% Galactose on Day 1.

A volume of 0.10 mL whole blood was collected via sublingual vein or jugular vein at each time-point at the following time points: Pre-Dose, Day 2 (1 hour after $3^{rd}$ dose), Day 4 (1 hour after $3^{rd}$ dose), Day 6 (1 hour after $3^{rd}$ dose), Day 8 (1 hour after $3^{rd}$ dose), and Day 10 (1 hour after $3^{rd}$ dose). Blood samples was allowed to clot for >30 minutes under ambient conditions, then was centrifuged at 22° C., 3000 RPM for 10 min. The collected serum was stored frozen at approximately −80° C. until analysis.

The data obtained in this study shown in FIG. 1 indicate that the evolved clone administered to rats resulted in a potent reduction of galactose in serum. Of note, administration via three daily oral gavages of high quantities of the evolved clone did not show apparent adverse effects. Thus, the evolved clone appears to be effective and safe at detoxifying galactose in food. Consequently, it could have beneficial effects in subjects suffering from consequences of diets with high content of galactose.

Example 8: Isolation and Identification of Yeast Strains for Fructose Metabolism A primary goal of the present invention was to develop yeast strains highly effective at metabolizing fructose. Yeasts were isolated from fructose-containing food such as grapevine berries. Various species were isolated by cultivating the samples in fructose-containing culture medium at room temperature for a period of time of at least 2 days. Isolates were then identified by a molecular approach based on targeted sequencing of Internal Transcribed Spacers (ITS). The isolates were then subjected to adaptive evolution to generate clones with superior fructose-detoxification performance.

Strains were isolated mainly from grapes from two sources: Sauvignon and Pinot Noir. The berries were collected into sterile flasks and after cultivation for approximately 2 weeks at laboratory temperature with an agitation of 125 rpm in liquid minimal medium CM (Synthetic Complete Minimal Medium, 0.5% Ammonium Sulfate, Teknova) with 50 ug/mL chloramphenicol (Teknova), cultures were serially diluted and seeded again in liquid medium with selection and incubated at 30° C. with agitation of 125 rpm. For selection, 4% fructose (Acros) was added to the medium with or without 2% glucose (Teknova) and 2% raffinose (Teknova). This cycle was performed at least 3 times until plating serially diluted cultures on YP plates (1% yeast extract, 2% peptone; Teknova) supplemented with 4% fructose. Single colonies obtained after incubation at 30° C. for 2-5 days were sequentially streaked multiple times to obtain pure isolates.

For taxonomy assignment, the targeted metagenomic sequencing method was employed. Briefly, the isolates were processed for DNA extraction using the ZymoBIOMICS®-96 MagBead DNA Kit and the DNA samples were prepared for targeted sequencing using targeted Internal Transcribed Spacers primer sets (ITS2, Zymo Research, Irvine, CA). The final library was sequenced on Illumina® MiSeg™. Taxonomy analyses were performed on publicly available sequences using the BLAST program under default settings (www-dot-ncbi-dot-nlm-dot-nih-dot-gov/BLAST).

The ITS sequences obtained from pool cultures and from isolate cultures were analyzed to identify isolate phylogeny. Table 10 reports the outcome of this analysis ("Hits") based on the homology of ITS sequences amplified from pool cultures and purified isolate cultures with publicly available sequences. The table lists the species exhibiting the greatest score and 100% sequence identity with ITS sequences obtained from this study.

parental strains isolated from grapes (See Çakar et al., "Evolutionary engineering of *Saccharomyces cerevisiae* for improved industrially important properties." FEMS Yeast Res 12:171-82 (2011). Cultures of various isolates were initiated from a single colony on agar plates or from glycerol stocks, and grown in liquid YP medium by incubation at 30° C. with agitation at 125 rpm (Murakami & Kaeberlein "Quantifying Yeast Chronological Life Span by Outgrowth of Aged Cells." J Visual Exp (27) (2009)). Parallel cultures were independently grown at 30° C. under agitation at 125 rpm in 15 mL CM medium in 50 mL vented tubes or 3 mL in 14 mL culture tubes supplemented with 2% fructose as a pressure selection agent for about 16 to 30 hours before

TABLE 10

Blast Results of Sequences Obtained after Amplification of Internal Transcribed Spacers (ITS) from Pool Cultures and from Isolate Cultures.

| Source | Hits |
| --- | --- |
| List of potential assignment for Pool_G1 isolated from grapes subjected to selection medium containing 4% fructose | *Pichia kudriavzevii, Pichia cecembensis, Pichia* sp. *Brettanoyces bruxellensis, Brettanomyces* sp. |
| Taxonomic assignment as per Blast search for isolate G1_1 derived from Pool_G1 culture | *Pichia kudriavzevii* |
| List of potential assignment for Pool_G2 isolated from grapes subjected to selection medium containing 4% fructose | *Saccharomyces* sp., *Saccharomyces cerevisiae. Saccharomyces uvarum, Saccharomyces eubayanus, Saccharomyces bayanus, Saccharomyces paradoxus, Saccharomyces jurei, Saccharomyces* sp. 'boulardii', *Saccharomyces kudriavzevii, Pichia* sp. |
| Taxonomic assignment as per Blast search for isolate G2_1 derived from Pool_G2 culture | *Saccharomyces cerevisiae* |
| List of potential assignment for Pool_G3 isolated from grapes subjected to selection medium containing 4% fructose | *Hanseniaspora* sp., *Hanseniaspora uvarum, Hanseniaspora opuntiae, Hanseniaspora thailandica, Limtongozyma cylindracea Saccharomyces* sp., *Saccharomyces cerevisiae, Saccharomyces uvarum* |
| Taxonomic assignment as per Blast search for isolate G3_1 derived from Pool_G3 culture | *Saccharomyces uvarum* |
| List of potential assignment for Pool_G4 isolated from grapes subjected to selection medium containing 4% fructose and 2% raffinose | *Metschnikowia* sp., *Metschnikowia peoriensis, Metschnikowia bicuspidata, Metschnikowia cibodasensis, Metschnikowia zobellii, Metschnikowia henanensis, Metschnikowia colchici, Metschnikowia noctiluminum, Metschnikowia rancensis, Metschnikowia maroccana, Metschnikowia vanudenii, Metschnikowia reukaufii, Metschnikowia koreensis, Metschnikowia cibodasensis, Metschnikowia peoriensis, Metschnikowia gelsemii, Metschnikowia bicuspidata, Metschnikowia henanensis, Metschnikowia zobellii, Metschnikowia gruessii, Metschnikowia chrysomelidarum, Metschnikowia colchici, Metschnikowia viticola, Metschnikowia kofuensis, Saturnispora zaruensis* |
| Taxonomic assignment as per Blast search for isolate G4_1 derived from Pool_G4 culture | Metschnikowia_reukaufii |

Example 9: Adaptive Evolution

Adaptive evolution was applied to yeast strains, a method that can increase traits of a given strain owing to random mutations in the genome. Clones derived from parental strains that offer a phenotypic advantage are naturally selected when grown under selective pressure. Yeast can be subjected to adaptive evolution with changes that can be observed in a short time period because yeast grows rapidly as single cells in simple media, with the entire life cycle completed in culture similarly to bacteria.

Adaptive evolution was carried out on the isolates by daily serial dilution conducted for at least 28 cycles of transferring the cultures to fresh medium at a 1:30 dilution. The procedure of serial dilution was repeated until a change in growth was detected by $OD_{600}$. A volume of 100 µL of a 1:1,000 dilution of the last daily serial dilution of the culture with the greatest OD was plated on YP-fructose agar medium and incubated at 30° C. Isolated, adaptively evolved clones were randomly selected from the plate to start duplicate cultures grown at 30° C. under agitation at 125 rpm in 3 mL CM medium supplemented with 4% fructose alone or 4% fructose and 0.5 to 2% glucose. After multiple rounds of screening tests evaluating growth and fructose consumption in presence or absence of glucose, several leads were selected. A typical example of data profiles is shown in the table below.

To assess the yeast strains' and clones' ability to degrade fructose, the concentration of fructose was determined using the colorimetric Fructose Assay Kit (Cat. No. EFRU-100; BioAssay Systems, Hayward, CA). All reactions were performed in 96-well microplates and the absorbance was read at 565 nm using volumes and concentrations recommended by the kit. The samples and standards were mixed with the enzyme fructose dehydrogenase, MTT [3-(4,5-dimethylthi-aze-syl)-2,5-diphenyltetrazolium bromide] and phenazine methosulfate (PMS), which reacts with fructose to produce a colored compound MTT formazan measurable by direct spectrophotometry. Sample concentrations were determined by comparison to a standard curve generated with known quantities of fructose.

Utilization and degradation of fructose was assessed by measuring fructose consumption by the strains. Table 11, below, lists the percentage of fructose reduction in spent culture medium for one adaptively evolved strain and the corresponding parent strain G4_1 when grown in presence of 4% fructose (=222 mM) and 1% glucose. This data set illustrates that the adaptively evolved clone was able to significantly degrade fructose. The evolved strain exhibited a reduction greater than 95% of fructose initial concentration compared to less than 5% reduction for the parental strain at the 3-hour time point for the same cell density. This difference is statistically significant, confirming that adaptive evolution produced a more efficient strain.

TABLE 11

Remaining Fructose Concentration (mM) after Exposure to a Solution of 4% Fructose and 1% Glucose with Parent Clone G4_1 and Evolved Clone G41A

| Clone | Parent G4_1 | G4_1A | G4_1A |
|---|---|---|---|
| Cell Density (CFU/mL) | 1.00E+09 | 1.00E+08 | 1.00E+09 |
| Time point: 0.2 hour | 193.70 mM (88.1%) | 168.57 mM (76.7%) | 134.51 mM (61.1%) |
| Time point: 2.0 hour | 214.26 mM (97.4%) | 112.22 mM (51.0%) | 29.97 mM (13.6%) |
| Time point: 3.0 hour | 212.88 mM (96.8%) | 114.98 mM (52.3%) | 5.98 mM (2.7%) |

Values between brackets indicate the percentage of fructose remaining when compared with the average value of the positive control (219.98 mM).
CFU—Colony Forming Unit.

Example 10: Degradation of Fructose in Food

As part of evaluating the feasibility of a yeast-based approach as a treatment to mitigate the effects of elevated concentrations of fructose in foods and beverages, several evolved clones obtained by adaptive evolution were tested for their ability of degrading fructose when present in food.

For this study, two evolved yeast strains obtained by adaptive evolution, G1_1A and G2_1A were tested for their ability to degrade dietary fructose. The testing of fructose consumption was started with yeast cells obtained from a culture initiated from a single colony on agar plates and grown in 15 mL of liquid YP medium in a 50-mL mini-bioreactor by incubation at 30° C. with an agitation of 225 rpm supplemented with 4% fructose. Cells were pelleted by centrifugation at 1000 rpm (Sorval, RT7) for 10 min at room temperature. Cell pellets were resuspended in 5 mL rodent diet (Teklad, Envigo) spiked with a solution of 10% fructose (=555 mM). Reactions were incubated at 37° C. to mimic human gastrointestinal temperature conditions. Aliquots of the reactions were taken at multiple time points and stored at −20° C. until fructose concentration determination using the colorimetric Fructose Assay Kit (Cat. No. EFRU-100; BioAssay Systems, Hayward, CA).

As shown in Table 12, the evolved clones were able to rapidly decrease fructose concentration when present in diet.

TABLE 12

Remaining Fructose (%) after Exposure for 0.5 to 3 Hours to a Solution of 10% Fructose with Evolved Clones G1_1A and G2_1A

| Clone | G1_1A | G1_1A | G1_1A | G2_1A | G2_1A | G2_1A |
|---|---|---|---|---|---|---|
| CFU/mL | 3.10E+09 | 6.21E+09 | 2.17E+10 | 3.39E+09 | 6.78E+09 | 2.37E+10 |
| Time point: 0.5 hr | 111.1% | 88.2% | 45.9% | 91.3% | 76.8% | 37.8% |
| Time point: 2.0 hr | 78.0% | 53.2% | 6.3% | 77.2% | 53.3% | 5.6% |
| Time point: 3.0 hr | 60.8% | 35.2% | −1.5% | 59.7% | 34.7% | −0.5% |

Example 11: Tolerance to Gastrointestinal Conditions

The most convenient way to deliver a yeast-based therapeutic is orally. During transit through the gastrointestinal tract, an orally delivered agent will be confronted to a variety of simultaneous or sequential adverse conditions, such as the internal body temperature, gastric fluid with acidic pH, and pancreatic fluid with alkaline fluid. A series of in vitro experiments were conducted to assess the potential for survival of the evolved clones when subjected to gastrointestinal conditions.

Yeast cells were subjected to simulated gastric fluid (SGF) supplemented with 1 mg/mL of pepsin and simulated intestinal fluid (SIF) supplemented with 1 mg/mL of pancreatin to evaluate their tolerance to gastrointestinal conditions. (Zhou et al. "Statistical investigation of simulated fed intestinal media composition on the equilibrium solubility of oral drugs." Eur J Pharm Sci 99:95-104 (2017). Overnight yeast cultures grown in liquid YP medium supplemented with 4% fructose were harvested by centrifugation for 10 min at 1000 rpm at room temperature. To test for survival in gastric fluid, pellets were re-suspended in 1 mL SGF (Cat No. 7108.16; RICCA Chemical Company, Arlington, Texas) supplemented with pepsin from porcine gastric mucosa with an activity of 8.60 European Units/mg (Cat No. 41707-1000; ACROS Organics, Geel, Belgium). The pH was measured (pH~1 to 2). Reactions were maintained at 37° C. and aliquots were taken at the indicated time points. To test for survival in intestinal fluid, cells were centrifuged for 10 min at 1000 rpm at room temperature and re-suspended in 1 mL SIF (RICCA Chemical Company, Cat No. 7109.16, pH 6.7-6.9 supplemented with 1 mg/mL of pancreatin from porcine pancreas (Sigma, Cat No. P3292). Reactions were maintained at 37° C. and aliquots were taken at the indicated time points. Yeast cells were counted before and after intestinal challenges with Simulated Gastric Fluid (SGF) and Simulated Intestinal Fluid (SIF). The survival rate was estimated by evaluating the ratio between cell counts of yeast preparations subjected to the simulated fluid challenge over time vs. the same preparations at time zero. Viable cell counts were determined using a hemocytometer and Trypan blue staining. Strain *Saccharomyces boulardii* (SB) was prepared similarly to the evolved clones except that it was grown in YP medium supplemented with 2% glucose.

As shown in Tables 13 and 14, the gastric environment had an impact on strain survival. For evolved clones G1_1A and clone G2_1A, SIF had minimal impact on cell counts and SGF reduced the cell count only after 180 min incubation.

TABLE 13

Survivability Time Course (%) of Four Evolved Clones in Gastrointestinal Conditions after Exposure to SGF over a Period of 90 min

| | Clone | | | | |
|---|---|---|---|---|---|
| | Clone G1_1A | Clone G2_1A | Clone G3_1A | Clone G4_1A | SB |
| 0 min | 100.0 | 100.0 | 100.0 | 98.5 | 100.0 |
| 90 min | 95.9 | 97.2 | 46.7 | 0 | 15.4 |

TABLE 14

Survivability Time Course (%) of Two Evolved Clones in Gastrointestinal Conditions after Exposure to Simulated Fluids over a Period of 180 min

| | Clone G1_1A | | | Clone G2_1B | | |
|---|---|---|---|---|---|---|
| Conditions | PBS | SGF | SIF | PBS | SGF | SIF |
| 0 min | 98.9 | 98.2 | 99.5 | 99.5 | 98.4 | 99.5 |
| 60 min | 99.5 | 98.1 | 99.5 | 99.5 | 95.5 | 99.5 |
| 120 min | 100.0 | 91.0 | 98.5 | 100.0 | 91.0 | 100.0 |
| 180 min | 98.9 | 66.7 | 99.4 | 98.9 | 65.2 | 99.5 |

SGF—Simulated Gastric Fluid;
SIF—Simulated Intestinal Fluid.

Example 12: Mitigation of Fructose Accumulation in Serum after a Single Oral Administration of the Evolved Clone The objective of this study was to assess the ability of the test article to detoxify fructose in vivo. To that end, serum fructose concentration was assessed after a single bolus oral administration to animals of 10% fructose and 20% fructose with or without concurrent administration of the test article.

Fifteen-week-old male Sprague-Dawley rats weighing between 350 and 400 g were acquired from Envigo with a catheter surgically implanted in the jugular vein. Animals were housed individually in polycarbonate cages containing animal bedding during the acclimation period lasting 7 days. Environmental controls were maintained at 18 to 23° C. with humidity of 30% to 70% with automatic lighting on a 12 h/12 h on/off cycle except as required for specimen collection and study conduct. Animals were fed an irradiated chow diet (Teklad, Envigo, CA) and were provided municipal tap water ad libitum. No concurrent medication was given. Animal care and procedures were approved by the Institutional Animal Care and Use Committee and were followed in accordance to the standards for animal husbandry and care of the U.S. Department of Agriculture's (USDA) Animal Welfare Act. Veterinary care was available throughout the course of the study and animals were examined by the veterinary staff as warranted.

The rats were randomly distributed into five groups, each consisting of three animals. Group I and Group II were administered with a solution of 10% (=555 mM) and 20% fructose, respectively; Group III was administered with the test article alone; Group IV and V were administered with a solution of 10% fructose and 20% fructose, respectively, together with the test article. All animals were fasted for a period of 16 hour prior to dosing and all animals were administered a single bolus dose of 10 mL/kg by oral gavage. The cell density of the test article (Evolved Clone G1_1A) was 4.0E+09 CFU/mL prepared from an overnight culture incubated at 30° C. in orbital shaker and grown in YP medium supplemented with 4% fructose. Blood samples (0.3 mL) were collected serially via catheterized jugular veins at 0 pre-dose and at 0.5, 1, 1.5, 2, 4, and 8-hour after dosing for analysis of fructose concentration in serum. All samples were stored frozen until analysis. Fructose levels in serum samples were determined using the EnzyChrom™ Fructose Assay Kit (BioAssay Systems, Hayward, CA) and analyzed in duplicate in a microplate reader (Molecular Devices).

Figure 2A:
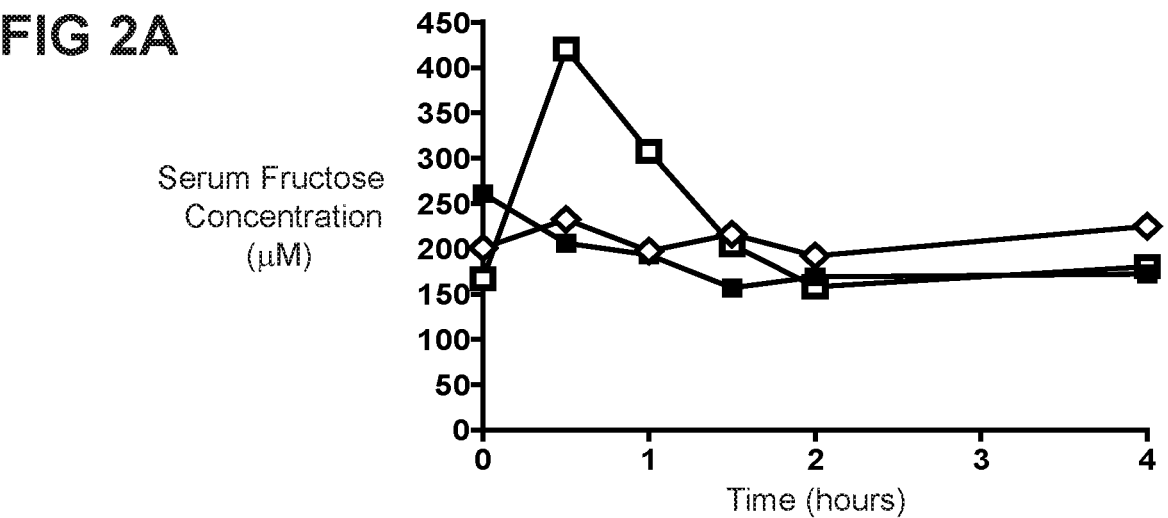
FIGS. 2A and 2B illustrate the time course profile of fructose concentrations (vertical axis, in μM) in serum of animals after oral administration of a single bolus dose of fructose with or without the test article.
Figure 2B:
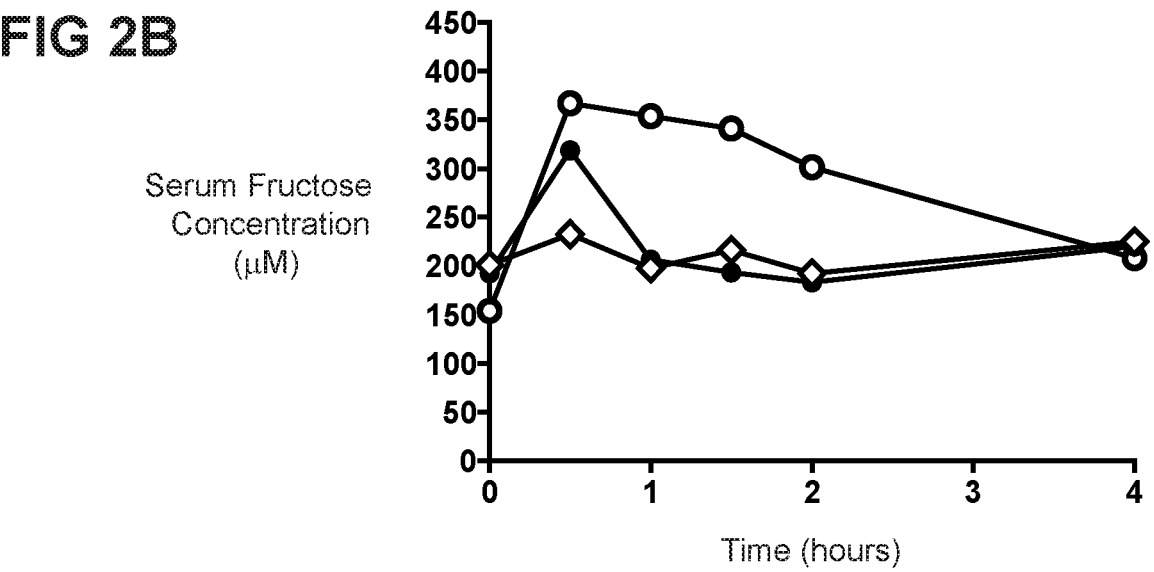

As shown in FIGS. 2A and 2B, fructose concentration rose sharply to a concentration of approximately 400 µM after administration of a single bolus dose of 10% fructose (555 mM) (FIG. 2A) or 20% fructose (1,110 mM) (FIG. 2B) and reached its peak level in serum 30 min after administration by oral gavage. Interestingly, for the group treated with the test article concurrently to fructose, the concentration of fructose in serum samples were lower than for the animals exposed to fructose alone. The data indicate that the strain administered to rats resulted in a potent reduction of fructose in serum. Thus, the strain appears to be effective at detoxifying fructose when delivered orally.

Example 13: Mitigation of Dietary Fructose Induced Symptoms after a Single Bolus Dose of Fructose A group of adult subjects who presents one or more symptoms such as abdominal bloating, flatulence, pain, distension, diarrhea and nausea within 2 to 8 hours after drinking a beverage containing 25 g fructose is administered an oral dose of the preparation of the invention prior to the fructose provocation. During the following 8 hours, multiple tests are performed including breath test and blood fructose concentration evaluation. It is observed that the administration of the preparation of the invention decreases the production of hydrogen gas in the respiratory air and it levels off blood fructose level rapidly. These data confirm that preparation of the invention can efficiently detoxify fructose.

Example 14: Mitigation of Dietary Fructose-Induced Symptoms by Multiple Doses of Preparation of the Invention An adult patient with dietary fructose intolerance presents with one or more of symptoms such as abdominal bloating, flatulence, pain, distension, diarrhea and nausea. Treatment with the preparation of the invention is initiated by the clinician at an effective dose, which mitigates fructose-induced symptoms. Assessment of symptoms and testing are periodically performed. The dose of the treatment is adjusted as required by the clinician in attendance to manage symptoms of the dietary fructose-related condition. The subject may be treated with other drugs concurrently and may or may not be under restricted diet. Treatment with the preparation of the present invention is able to mitigate one or more symptoms related to dietary fructose.

What is claimed is:

1. A method for treating galactosemia or dietary intolerance of galactose, in a subject, comprising:
   administering to the subject with galactosemia or dietary intolerance of galactose an effective amount of an adaptively evolved microorganism to the subject wherein the effective amount of the adaptively evolved microorganism reduces the amount of the galactose in the presence of glucose.

2. The method of claim 1, wherein the effective amount of the adaptively evolved microorganism is administered to the subject in food containing an amount of galactose that the subject does not tolerate.

3. The method of claim 2, wherein the food further contains glucose, lactose or both glucose and lactose.

4. The method of claim 1, wherein the adaptively evolved microorganism is a yeast that degrades galactose in the presence of glucose.

5. The method of claim 4, wherein the yeast is selected from the group consisting of a *Saccharomyces* sp., a *Kluyveromyces* sp., a *Pichia* sp., and a *Metschnikowia* sp.

6. The method of claim 4, wherein the yeast is selected from the group consisting of *Saccharomyces cerevisiae, Saccharomyces uvarum, Kluyveromyces marxianus, Pichia kudriavzevii,* and *Metschnikowia reukaufii*.

7. The method of claim 6, wherein the adaptively evolved microorganism is *Saccharomyces cerevisiae* strain Y_C202_1 (Accession No. NRRL Y-67930), *Saccharomyces cerevisiae* strain Y_C201_1 (Accession No, NRRL Y-6793 1), or *Kluyveromyces marxianus* strain K_219 (Accession No NRRL Y-67932).

* * * * *